Oct. 6, 1942. T. J. MORRIS Plant Pat. 546
ROSE PLANT
Filed March 17, 1942
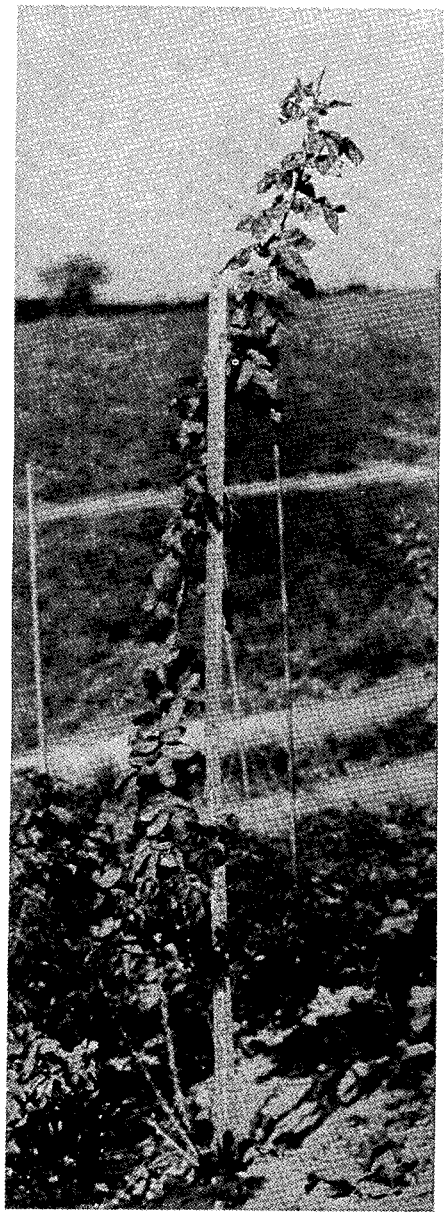
Inventor
T. J. Morris
By Robb & Robb
Attorneys Patented Oct. 6, 1942

UNITED STATES PATENT OFFICE

546

ROSE PLANT

Theodore J. Morris, San Fernando, Calif., assignor to Jackson & Perkins Company, Newark, N. Y.

Application March 17, 1942, Serial No. 435,090

1 Claim. (Cl. 47—61)

The present discovery relates to a new and distinct variety of rose plant, originating as a sport of Floribunda "World's Fair" observed by me growing upon its parent bush.

This new variety is distinguished from its parent variety primarily by its climbing habit, that is, the habit of sending up long, strong shoots which in turn send out blooming spikes continuously like any other climbing rose.

This new rose is further notable for the repeating bloom which occurs on the blooming spike, in this respect being unique and different from any other climbing rose.

It may be noted that this new rose has the same general form and color as its parent, and therefore no claim is made regarding the color features.

The following is a detailed description of the new variety, color terminology being in accord with Ridgway's Color Standard:

Parentage: Sport.

*Parent variety.*—"World's Fair."

Classification: Botanic and commercial—everblooming climber.

*Flower*

(Observations made in the morning of September 28, 1941, at Newark, New York.)

Blooming habit: Recurrent—continuous.

Bud:

*Size.*—Medium.

*Form.*—Urn. Is not affected by wet or hot weather.

*Color.*—When sepals first divide—Oxblood Red, Plate 1. When petals begin to unfurl—between Oxblood Red, Plate 1, and Carmine, Plate 1. When half blown, inside of petals—Carmine, Plate 1. Reverse of petals—Pomegranate Purple, Plate 12.

*Sepals.*—Smooth edge. Curl back in early stages as flower opens.

*Calyx.*—*Shape*—apple. *Size*—small. *Aspect*—smooth.

*Peduncle.*—*Length*—long. *Aspect*—smooth. *Color*—Brownish Olive, Plate 30. *Strength*—erect.

*Opening.*—Bud opens well. Is not affected by adverse conditions.

Bloom:

*Size.*—Medium. Average size when fully expanded—four inches.

*Borne.*—In clusters, irregular.

*Stems.*—Long; strong.

*Form.*—When first open—cupped. *Permanence*—flattens.

*Petalage.*—Double (full but open center). Number of petals under normal conditions—18.

*Color.*—Center of flower—between Oxblood Red, Plate 1, and Carmine, Plate 1. Outer petals—between Carmine, Plate 1, and Spectrum Red, Plate 1. Base of petals (aiglet)—Pinard Yellow, Plate 4. Inside of petals—between Carmine, Plate 1, and Oxblood Red, Plate 1. Reverse of petals—Carmine, Plate 1. General tonality from a distance—Scarlet Red, Plate 1.

*Discoloration.*—General tonality at end of first day—Oxblood Red, Plate 1, to Carmine, Plate 1. Second day—Carmine, Plate 1. Third day—Carmine, Plate 1.

Petals:

*Texture.*—Thick. Is not affected by wet or hot weather.

*Appearance.*—Inside—velvety. Outside—shiny.

*Form.*—Notched.

*Arrangement.*—Informal (with "rags" in center). Petaloids in center—few; small.

*Persistence.*—Drop off cleanly.

*Fragrance.*—Moderate. Nature—tea (average hybrid tea scent).

*Lasting quality.*—On the plant—long. As cut flower—fair.

Genital organs:

*Stamens, anthers.*—*Size*—large. *Color*—Yellow Ocher, Plate 15. *Arrangement*—regular around styles.

*Stamens, filaments (threads).*—*Length*—medium. *Color*—Light Jasper Red, Plate 13.

*Pollen.*—Zinc Orange, Plate 15.

*Styles.*—Bunched; medium length; heavy.

*Stigmas.*—Pinard Yellow, Plate 4.

*Ovaries.*—All enclosed in calyx.

Fruit: variety is fertile with its own pollen.

*Form.*—Depressed top.

*Aspect.*—Smooth.

*Sepals.*—Caducous (soon falling).

*Plant*

Form: Climber.

Growth: Eight to ten feet shoots.

Foliage: Five to seven leaflets.

*Size.*—Large.

*Quantity.*—Abundant.

*Color.*—New foliage: upper side—Maroon, Plate 1; under side—Madder Brown, Plate 13. *Old foliage*: upper side—Dark Cress Green, Plate 31; under side—Light Cress Green, Plate 31.

*Shape.*—Oval pointed.

*Texture.*—Upper side—leathery. Under side—rough. *Ribs and veins*—ordinary.
*Edge.*—Serrated (saw-toothed).
*Serration.*—Single; large.
*Rachis.*—*Color*—Light Cress Green, Plate 31; under side—smooth.
*Stipules.*—Medium length; bearded.
*Disease resistance.*—Resistant.

Wood:
*New wood.*—*Color*—Vandyke Red, Plate 13. *Bark*—smooth.
*Old wood.*—*Color*—Cress Green, Plate 31. *Bark*—smooth.

Thorns:
*Thorns.*—*Quantity*—on main stalks from base and on laterals from stalk—few. *Form*—narrow base; medium length; hooked downward. *Color when young*—Hessian Brown, Plate 13. *Position*—in pairs.
*Prickles.*—*Quantity*—on main stalks and on laterals—few. *Color*—Hessian Brown, Plate 13.
*Short needles.*—*Quantity*—on main stalks and on laterals—none.

I claim:

A new and distinct variety of rose plant, characterized as to novelty by its climbing habit, and repeating bloom occurring on the blooming spike, substantially as shown and described.

THEODORE J. MORRIS.